United States Patent [19]

Greig

[11] 3,973,037
[45] Aug. 3, 1976

[54] HYDRATROPIC ACID DERIVATIVES IN THE TREATMENT OF NON-INFLAMMATORY ALLERGIC REACTIONS

[75] Inventor: Margaret E. Greig, Kalamazoo, Mich.

[73] Assignee: The Upjohn Company, Kalamazoo, Mich.

[22] Filed: Feb. 7, 1975

[21] Appl. No.: 547,922

Related U.S. Application Data

[63] Continuation-in-part of Ser. No. 479,213, June 14, 1974, Pat. No. 3,865,949, which is a continuation-in-part of Ser. No. 384,819, Aug. 2, 1973, abandoned, which is a continuation of Ser. No. 258,353, May 31, 1972, abandoned.

[52] U.S. Cl. .............................................. 424/317
[51] Int. Cl.² ....................................... A61K 31/19
[58] Field of Search ................................... 424/317

[56] References Cited
UNITED STATES PATENTS
3,452,079 6/1969 Shen et al. ...................... 424/317

OTHER PUBLICATIONS
Merck Manual, 12th Edition, 1972, pp. 1252–1255.
Chemical Abstracts, vol. 64, 5005e (1966).

Primary Examiner—Norman A. Drezin
Attorney, Agent, or Firm—John J. Killinger; Roman Saliwanchik

[57] ABSTRACT

A process for the therapeutic treatment of allergy by the systemic administration of a compound of the formula:

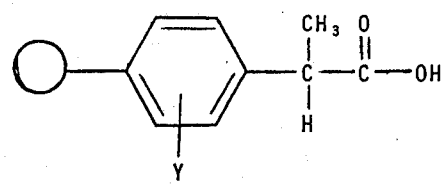

(Formula I)

wherein

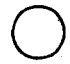

is cyclohexane or

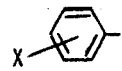

and X and Y can be the same or different and are hydrogen, fluoro, chloro, bromo, alkyl of from 1 to 8 carbon atoms, inclusive, or alkoxy of from 1 to 8 carbon atoms, inclusive, and the pharmacologically acceptable salts thereof in association with a pharmaceutical carrier.

5 Claims, No Drawings

HYDRATROPIC ACID DERIVATIVES IN THE TREATMENT OF NON-INFLAMMATORY ALLERGIC REACTIONS

CROSS REFERENCE TO RELATED APPLICATIONS

This application is a continuation-in-part of application Ser. No. 479,213, filed June 14, 1974, now U.S. Pat. No. 3,865,949, said patent being a continuation-in-part of application Ser. No. 384,819, filed Aug. 2, 1973, now abandoned, which in turn is a continuation of application Ser. No. 258,353, filed May 31, 1972, now abandoned.

BRIEF DESCRIPTION OF THE INVENTION

This invention relates to a novel method for therapeutic treatment of allergic conditions by the systemic administration of a compound of the Formula I to a human or animal subject.

DETAILED DESCRIPTION OF THE INVENTION

The compounds of the Formula I are old compounds known in the art. The compounds are depicted in the protonated or acid form, however, for the purposes of the instant invention the proton can be replaced by any pharmacologically acceptable cation.

The compounds have optical isomerism and for the purposes of the instant invention the $d$ and $dl$ forms are preferred.

The compositions of the present invention are presented for administration to humans and animals in unit dosage forms, such as tablets, capsules, pills, powders, granules, sterile parenteral solutions or suspensions, and oral solutions or suspensions, and oil-in-water and water-in-oil emulsions containing suitable quantities of the compound of Formula I. Another route of administration is by inhalation into the lung by means of an aerosol or powder for insufflation.

For oral administration either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with a syrup vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Compositions for inhalation are of three basic types: (1) a powder mixture preferably micro-pulverized; (2) an aqueous solution to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula I in water and adding salt to provide an isotonic solution and buffering to a pH compatible with inhalation. The solutions are dispersed in a spray device or nebulizer and sprayed into the mouth while inhaling.

Aerosols are prepared by dissolving a compound of the Formula I in water or ethanol and mixing with a volatile propellant and placing in a pressurized container having a metering valve to release a predetermined amount of material.

The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, granules, wafers, cachets, teaspoonfuls, tablespoonfuls, dropperfuls, ampuls, vials, aerosols with metered discharges, segregated multiples of any of the foregoing, and other forms as herein described.

The dosage of the compound for treatment depends on the route of administration. A dosage schedule of from about 5 to 200 mg. in a single dose administered orally, parenterally or by inhalation, embraces the effective range for treating allergic attack for which the compositions are effective. The dosage to be administered is repeated up to 4 times daily.

The administration of the compositions of the present invention to humans and animals provides a method for the therapeutic treatment of non-inflammatory allergic reactions.

Non-inflammatory allergic reactions in this application are of the Type I immediate type. Such reactions are usually, but not always, mediated by the presence of antibodies attached to mast cells, such that when an antigen is presented to the tissue-bound antibody a combination results leading to the release of one or more mediators of anaphyloxies (histamine, SRSA, bradykinin, and prostaglandins) which then react at some end organ receptor to cause the symptoms of the disease. Specific disease entities within the foregoing definition are (but not limited to) asthma; food allergy; certain drug allergies; and allergic rhinitis (hay fever).

The following examples are illustrative of the process and products of the present invention but are not to be construed as limiting.

EXAMPLE 1

A lot of 10,000 tablets, each containing 20 mg. of 3-fluoro-4-phenylhydratropic acid is prepared from the following types and amounts of ingredients:

| | |
|---|---|
| 3-fluoro-4-phenylhydratropic acid | 200 gm. |
| Dicalcium phosphate | 1,500 gm. |
| Methylcellulose, U.S.P. (15 cps.) | 60 gm. |
| Talc | 150 gm. |
| Corn starch | 200 gm. |
| Calcium stearate | 12 gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in treating hay fever attacks at a dose of 1 tablet every four hours.

EXAMPLE 2

One thousand two-piece hard gelatin capsules, each containing 30 mg. of 3-fluoro-4-phenylhydratropic acid are prepared from the following types and amounts of ingredients:

| | |
|---|---|
| 3-fluoro-4-phenylhydratropic acid | 30 gm. |
| Talc | 100 gm. |
| Magnesium stearate | 10 gm. |

The ingredients are mixed well and filled into capsules of the proper size.

Capsules so prepared are useful in treating bronchial asthma at a dose of one capsule every six hours.

EXAMPLE 3

One thousand tablets, each containing 50 mg. of 3-fluoro-4-phenylhydratropic acid are made from the following types and amounts of ingredients:

| | |
|---|---|
| 3-fluoro-4-phenylhydratropic acid | 50 gm. |
| Microcrystalline cellulose NF | 120 gm. |
| Starch | 16 gm. |
| Magnesium stearate powder | 4 gm. |

The ingredients are screened and blended together and pressed into 50 mg. tablets.

The tablets are useful to treat food allergy at a dose of 1 tablet before meals.

EXAMPLE 4

A sterile preparation suitable for intramuscular injection and containing 10 mg. of 3-fluoro-4-phenylhydratropic acid in each milliliter is prepared from the following ingredients:

| | |
|---|---|
| 3-fluoro-4-phenylhydratropic acid | 10 gm. |
| Benzyl benzoate | 200 ml. |
| Methylparaben | 1.5 gm. |
| Propylparaben | 0.5 gm. |
| Cottonseed oil q.s. | 1,000 ml. |

One milliliter of this sterile preparation is injected for treatment of allergic rhinitis.

EXAMPLE 5

Aqueous Solution 600 ml. of an aqueous solution containing 50 mg. of sodium salt of 3-fluoro-4-phenylhydratropic acid is prepared as follows:

| | |
|---|---|
| Sodium salt of 3-fluoro-4-phenylhydratropic acid | 60 mg. |
| Sodium chloride | 5,400 mg. |
| Water for injection q.s. | 600 ml. |

The sodium chloride and 3-fluoro-4-phenylhydratropic acid are dissolved in sufficient water to make 600 ml. and sterile filtered.

The solution is placed in nebulizers designed to deliver 0.25 ml. of solution per spray.

The solution is sprayed (inhaled) into the lungs every 4 hours for treating asthma.

EXAMPLE 6

Powder for Insufflation

A powder mixture consisting of 100 mg. of 3-fluoro-4-phenylhydratropic acid and sufficient lactose to make 5 gm. of mixture is micropulverized and placed in an insufflator designed to deliver 50 mg. of powder per dose.

The powder is inhaled into the lungs for treating asthma.

EXAMPLE 7

Aerosol

Twelve grams of an aerosol composition is prepared from the following ingredients:

| | | |
|---|---|---|
| 3-fluoro-4-phenylhydratropic acid | 2.0 | gm. |
| Absolute ethanol | 4.855 | gm. |
| Freon 12 | 1.43 | gm. |
| Freon 114 | 5.7 | gm. |

The 3-fluoro-4-phenylhydratropic acid is dissolved in the ethanol and chilled to −30° C. and added to the chilled Freons. The 12 grams of composition is added to a 13 cc. plastic coated bottle and capped with a metering valve. The metering valve released 80 mg. of composition in an aerosol.

The aerosol is inhaled every 6 hours for treating of asthma.

EXAMPLE 8

Following the procedure of the preceding Examples 1–7, inclusive, substituting an equimolar amount of each of 3-chloro-4-cyclohexylhydratropic acid, 3-bromo-4-phenylhydratropic acid and 4-(o-fluorophenyl)hydratropic acid for the 3-fluoro-4-phenylhydratropic acid of the example, compositions are similarly prepared.

I claim:

1. A process for the therapeutic treatment of a non-inflammatory allergic reaction selected from the group consisting of allergic rhinitis, food allergy and drug allergy in a human suffering therefrom comprising the systemic administration to said human of from 15 to 200 mg. of a compound of the formula:

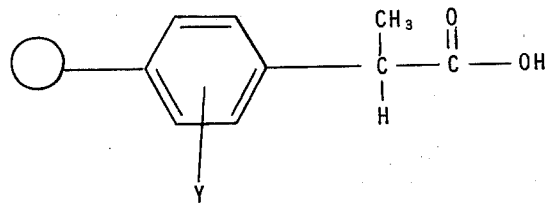

wherein

is cyclohexane or

and X and Y can be the same or different and are hydrogen, fluoro, chloro, bromo, alkyl of from 1 to 8 carbon atoms, inclusive, or alkoxy of from 1 to 8 carbon atoms, inclusive, and a pharmacologically acceptable salt thereof in association with a pharmaceutical carrier.

2. The process of claim 1 wherein the compound selected is the *d* or *dl* form of 3-fluoro-4-phenylhydratropic acid.

3. The process of claim 1 wherein the compound selected is the *d* or *dl* form of 3-chloro-4-cyclohexylhydratropic acid.

4. The process of claim 1 wherein the compound selected is the *d* or *dl* form of 3-bromo-4-phenylhydratropic acid.

5. The process of claim 1 wherein the compound selected is the *d* or *dl* form of 4-(o-fluorophenyl)hydratropic acid.

* * * * *